(12) United States Patent
Evans et al.

(10) Patent No.: US 7,041,447 B2
(45) Date of Patent: May 9, 2006

(54) HAPLOTYPING METHOD FOR MULTIPLE DISTAL NUCLEOTIDE POLYMORPHISMS

(75) Inventors: William Edward Evans, Cordova, TN (US); Oliver Gene McDonald, Charlottesville, VA (US)

(73) Assignee: St. Jude Children's Hospital, Inc., Memphis, TN (US)

( * ) Notice: Subject to any disclaimer, the term of this patent is extended or adjusted under 35 U.S.C. 154(b) by 394 days.

(21) Appl. No.: 09/829,113

(22) Filed: Apr. 9, 2001

(65) Prior Publication Data

US 2002/0081598 A1     Jun. 27, 2002

(51) Int. Cl.
    *C12Q 1/68*     (2006.01)
    *C12P 19/34*     (2006.01)

(52) U.S. Cl. .......................................... 435/6; 435/91.2
(58) Field of Classification Search ................ 435/6, 435/91.1, 91.2, 91.21; 536/23.1, 24.3
See application file for complete search history.

(56) References Cited

U.S. PATENT DOCUMENTS

2002/0025530 A1     2/2002     Affourtit et al.

OTHER PUBLICATIONS

Patel et al, "Direct haplotype determination by double ARMS: specificity, sensitivity and genetic applications", Nucleic Acids Res. (1991) 13:3561-3567.*
Michalatos-Beloin et al, "Molecular haplotyping of genetic markers 10kb apart by allele specific long-range PCR", Nucleic Acids Research (1996) 24:4841-4843.*
Krynetski et al, "A single point mutation leading to loss of catalytic activity in human thiopurine s-methyltransferase", Proc. Natl. Acad. Sci. (1995) 92:949-953.*
Martin et al, "SNPing away at complex diseases: analysis of single-nucleotide polymorphisms around APOe in Alzheimer disease", Am. J. Hum. Genet. (2000) 67:83-94.*
Li et al, "Allele specific, inverse PCR amplification for genotyping MN blood group", Biotechniques (1998) 25(3):358, 360, 361).*
Benkel, B., et al., "Long Range-inverse PCR (LR-IPCR): Extending the Useful Range of Inverse PCR," *Genetic Analysis: Biomolecular Engineering*, 1996, pp. 123-127, vol. 13.
Krynetski, E., et al., "A Single Point Mutation Leading to Loss of Catalytic Activity in Human Thiopurine S-Methyltransferase," *Proc. Natl. Acad. Sci. USA*, Feb. 1995, pp. 949-953, vol. 92.
Lo, Y-MD., et al., "Direct Haplotype Determination by Double ARMS: Specificity, Sensitivity and Genetic Applications," *Nucleic Acids Research*, 1991, pp. 3561-3567, vol. 19, No. 13.
Martin, E., et al., "SNPing Away at Complex Diseases: Analysis of Single-Nucleotide Polymorphisms Around APOE in Alzheimer Disease," *Am. J. Hum. Genet.*, 2000, pp. 383-394, vol. 67.
McDonald, O., et al., "Molecular Haplotyping of Genomic DNA for Multiple Single-Nucleotide Polymorphisms Located Kilobases Apart Using Long-range Polymerase Chain Reaction and Intramolecular Litigation," *Pharmacogenetics*, 2002, pp. 93-99, vol. 12, No. 2.
Michalatos-Beloin, S., et al., "Molecular Haplotyping of Genetic Markers 10 kb Apart by Allele-Specific Long-Range PCR," *Nucleic Acids Research*, 1996, pp. 4841-4843, vol. 24, No. 23.
Triglia, T., et al., A Procedure for *In Vitro* Amplification of DNA Segments That Lie Outside the Boundaries of Known Sequences, *Nucleic Acid Research*, 1988, p. 8186, vol. 16, No. 16.
Cheng, Suzanne et al., "Effective Amplification of Long Targets from Cloned Inserts and Human Genomic DNA", *Proc. Natl. Acad. Sci. USA*, Jun. 1994, pp. 5695-5699, vol. 91, National Academy of Science, DC USA.

(Continued)

*Primary Examiner*—Jeffrey Fredman
(74) *Attorney, Agent, or Firm*—Alston & Bird LLP

(57) ABSTRACT

The invention relates to methods for detecting genetic polymorphisms in an organism, particularly to the detection of genetic polymorphisms that are due to multiple distal nucleotide polymorphisms within a gene. Methods are provided for determining the haplotype structure of a gene, or other contiguous DNA segment, having two or more nucleotide polymorphisms that are separated by kilobases of DNA. The methods involve the use of PCR amplification and DNA ligation to bring the nucleotide polymorphisms on a particular allele of the gene into close proximity to facilitate the determination of haplotype structure.

20 Claims, 1 Drawing Sheet

OTHER PUBLICATIONS

Coco, Wayne M. et al., "DNA Shuffling Method for Generating Highly Recombined Genes and Evolved Enzymes", *Nature Biotechnology*, Apr. 2001, pp. 354-359, Nature America, Inc., New York, NY USA.

Collins, Francis S. and Weissman, Sherman M., "Directional Cloning of DNA Fragments at a Large Distance from an Initial Probe: A Circularization Method", *Proc. Natl. Acad. Sci. USA*, Nov. 1984, pp. 6812-6816, vol. 81, National Academy of Science, DC USA.

Conner, Brenda J. et al., "Detection of Sickle Cell $\beta^5$-globin Allele by Hybridization with Synthetic Oligonucleotides", *Proc. Natl. Acad. Sci. USA*, Jan. 1983, pp. 278-282, vol. 80, National Academy of Science, D.C. USA.

Michalatos-Beloin, Sonia et al., "Molecular Haplotyping of Genetic Markers 10 kb Apart by Allele-Specific Long-Range PCR", *Nucleic Acids Research*, 1996, pp. 4841-4843, vol. 24, No. 23, Oxford University Press, UK.

Nickerson, Deborah A. et al., "Automated DNA Diagnostics Using an ELISA-Based Oligonucleotide Litigation Assay" *Proc. Natl. Acad. Sci. USA*, Nov. 1990, pp. 8923-8927, vol. 87, National Academy of Science, DC USA.

Orita, Masato et al., "Detection of Polymorphisms of Human DNA by Gel Electrophoresis as Single-Strand Conformation Polymorphisms", *Proc. Natl. Acad. Sci. USA*, Apr. 1989, pp. 2766-2770, vol. 86, National Academy of Science, DC USA.

Prior, Thomas W. et al., "Rapid DNA Haplotyping Using a Multiplex Heteroduplex Approach: Application to Duchenne Muscular Dystrophy Carrier Testing", *Human Mutation*, 1995, pp. 263-268, vol. 5, Wiley-Liss, Inc., New York, NY.

Ruano, Gualberto and Kidd, Kenneth K., "Direct Haplotyping of Chromosomal Segments from Multiple Heterozgotes Via Allele-Specific PCR Amplification", *Nucleic Acids Research*, 1989, p. 8392, vol. 17, No. 20, IRL Press, Oxford UK.

Ruano, Gualberto et al., "Halotype of Multiple Polymorphisms Resolved by Enzymatic Amplification of Single DNA Molecules", *Proc. Natl. Acad. Sci. USA*, Aug. 1990, pp. 6296-6300, vol. 87, National Academy of Science, DC USA.

Ruano, Gualberto and Kidd, Kenneth K., "Genotyping and haplotyping of Polymorphisms Directly from Genomic DNA Via Coupled Amplification and Sequencing (CAS)", *Nucleic Acids Research*, Dec. 25, 1991, pp. 6877-6882, vol. 19, No. 24, IRL, Oxford, UK.

\* cited by examiner

SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: synthetic oligonucleotide primer
<221> NAME/KEY: misc_feature
<222> LOCATION: (3)..(8)
<223> OTHER INFORMATION: BamHI site

<400> SEQUENCE: 1
gcggatccga ggctgctgcc acaggctcct aaaac           35

-continued

```
<210> SEQ ID NO 2
<211> LENGTH: 40
<212> TYPE: DNA
<213> ORGANISM: Artificial Sequence
<220> FEATURE:
<223> OTHER INFORMATION: synthetic oligonucleotide primer
<221> NAME/KEY: misc_feature
<222> LOCATION: (3)..(8)
<223> OTHER INFORMATION: BamHI site

<400> SEQUENCE: 2
gcggatccca ctccaggttg ggcaacaaga acgaaactcc                                40

<210> SEQ ID NO 3
<211> LENGTH: 25
<212> TYPE: DNA
<213> ORGANISM: Homo sapiens

<400> SEQUENCE: 3
caagccttat agccttacac ccagg                                                25

<210> SEQ ID NO 4
<211> LENGTH: 23
<212> TYPE: DNA
<213> ORGANISM: Homo sapiens

<400> SEQUENCE: 4
gagacagagt ttcaccatct tgg                                                  23
```

HAPLOTYPING METHOD FOR MULTIPLE DISTAL NUCLEOTIDE POLYMORPHISMS

FEDERALLY SPONSORED RESEARCH OR DEVELOPMENT

This invention was made in part with U.S. Government support under National Institutes of Health grants GM 61393, R37 CA36401 and R01 CA78224, and Cancer Center support grant CA21765. The Government may have certain rights in this invention.

FIELD OF THE INVENTION

The invention relates to methods for detecting genetic polymorphisms in an organism, particularly to the detection of genetic polymorphisms that are due to multiple, single nucleotide polymorphisms within a gene.

BACKGROUND OF THE INVENTION

Genetic polymorphisms are well recognized mechanisms underlying inter-individual differences in disease risk and treatment response in humans (Evans and Relling (1999) Science 286:487–491; Shields and Harris (2000) J. Clin. Onc. 18:2309–2316). For many genes, the detection of single nucleotide polymorphisms (SNPs) known to confer loss of function provides a simple molecular diagnostic to select optimal medications and dosages for individual patients (Evans and Relling (1999) Science 286:487–491). However, it is quite common for genes to contain multiple SNPs, with haplotype structure being the principal determinant of phenotypic consequences (Collins et al. (1997) Science 278, 1580–81; Drysdale et al. (2000) Proc. Natl. Acad. Sci. 97:10483–8; Krynetski and Evans (1998) Am. J. Hum. Gen. 63:11–16). Therefore, to more accurately associate disease risks and pharmacogenomic traits with genetic polymorphisms, reliable methods are needed to unambiguously determine haplotype structure for multiple SNPs within a polymorphic gene.

Haplotype structure has been traditionally deduced by family pedigree analyses, but molecular haplotyping represents a more definitive approach that can be performed on individual patients, does not require parental information, and is not as labor-intensive as pedigree analyses. A variety of molecular methods, ranging in cost, complexity and availability, are currently used to haplotype intragenic SNPs. However, all widely available methods that do not involve cloning or physical separation of chromosomes are limited in their ability to accurately haplotype multiply heterozygous SNPs that are separated by kilobase distances within a gene.

Approaches that can be used to haplotype SNPs that reside within relatively close proximity include, but are not limited to, single-strand conformational polymorphism (SSCP) analysis (Orita et al. (1989) Proc. Natl. Acad. Sci. USA 86:2766–2770), heteroduplex analysis (Prior et al. (1995) Hum. Mutat. 5:263–268), and oligonucleotide ligation (Nickerson et al. (1990) Proc. Natl. Acad. Sci. USA 87:8923–8927) and hybridization assays (Conner et al. (1983) Proc. Natl. Acad. Sci. USA 80:278–282). A major drawback to these procedures is that they are limited to SNP detection along short segments of DNA and typically require stringent reaction conditions and/or labeling. Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296–6300), and coupled amplification and sequencing (CAS) (Ruano and Kidd (1991) Nucleic Acids Res. 19:6877–6882), are easily performed and highly sensitive, but these are also limited to haplotyping SNPs along short DNA segments (<1 kb) (Michalatos-Beloin et al. (1996) Nucleic Acids Res. 24:4841–4843; Barnes (1994) Proc. Natl. Acad. Sci. USA 91:5695–5699; Ruano and Kidd (1991) Nucleic Acids Res. 19:6877–6882).

Long-range PCR (LR-PCR) offers the potential to haplotype SNPs that are separated by kilobase lengths of genomic DNA. LR-PCR products are commonly genotyped for such SNPs, and haplotypes inferred using mathematical approaches (e.g., Clark's algorithm (Clark (1990) Mol. Biol. Evol. 7:111–122). However, inferring haplotypes in this manner does not yield unambiguous haplotype assignment when individuals are heterozygous at two or more loci (Hodge et al. (1999) Nature Genet. 21:360–361). Physically separating alleles by cloning, followed by sequencing, eliminates any ambiguity, but this method is laborious and expensive. Long-range allele-specific amplification negates both of these problems, but is limited to SNP-containing alleles that have heterozygous insertion/deletion anchors for PCR primers (Michalatos-Beloin et al. (1996) Nucleic Acids Res. 24:4841–4843). More complex technologies have also been used, such as monoallelic mutation analysis (MAMA) (Papadopoulos et al. (1995) Nature Genet. 11:99–102) and carbon nanotube probes (Woolley et al. (2000) Nature Biotech. 18:760–763), but these are either time consuming (MAMA), or require technology that is not widely available (nanotubes).

Thus, a simpler method for haplotyping SNPs separated by kilobase distances is needed to facilitate the analysis of haplotype structure in pharmacogenomic, disease pathogenesis, and molecular epidemiological studies.

SUMMARY OF THE INVENTION

The invention provides methods for determining the haplotype structure of genes, particularly genes with two or more nucleotide polymorphisms (NPs) that are separated by kilobase distances. The methods of the invention can be used to bring distantly spaced NPs on a contiguous DNA segment, particularly on the same allele of a gene, into much closer proximity than found in the native DNA segment or allele. By bringing the NPs into closer proximity, analysis of haplotype structure can be achieved by methods known in the art, which could not previously be employed in determining the haplotype structure of DNA segments and genes with distantly spaced NPs.

The method involves first obtaining a contiguous DNA segment having at least two NPs via polymerase chain reaction (PCR) amplification of a DNA sample. The contiguous DNA segment comprises, in the 5'-to-3' direction, a first NP, an intervening DNA sequence, and a second NP. The PCR amplification involves two oligonucleotide primers that are designed to anneal to regions adjacent to the NPs. The first primer is capable of annealing to a region adjacent to the first NP and distal to the second NP. Similarly, the second primer is capable of annealing to a region adjacent to the second NP and distal to the first NP. The first DNA fragment is circularized by intramolecular ligation to produce a circular DNA molecule. Thus, the intervening sequence lying between the NPs in the native gene is eliminated, and replaced with a much shorter sequence that includes both of the PCR primer sequences linked together. The methods of the invention, therefore, can be used to bring distantly spaced NPs into closer proximity on a circular DNA molecule, allowing haplotype structure to be determined by standard molecular haplotyping methods that are known in the art, including, but not limited to, restriction fragment-length polymorphism (RFLP) analysis, single-strand conformational polymorphism analysis, heteroduplex analysis, oligonucleotide ligation, hybridization assays, PCR-RFLP, allele-specific amplification, single-molecule dilution, coupled amplification and sequencing, and the like.

Additionally provided are kits for determining the haplotype structure of particular genes. The kits comprise specific oligonucleotide primers for amplifying portions of contiguous DNA segments comprising two or more NPs, thermostable DNA polymerases, and means for detecting the haplotype structure of each NP.

DETAILED DESCRIPTION OF THE INVENTION

Figure 1:
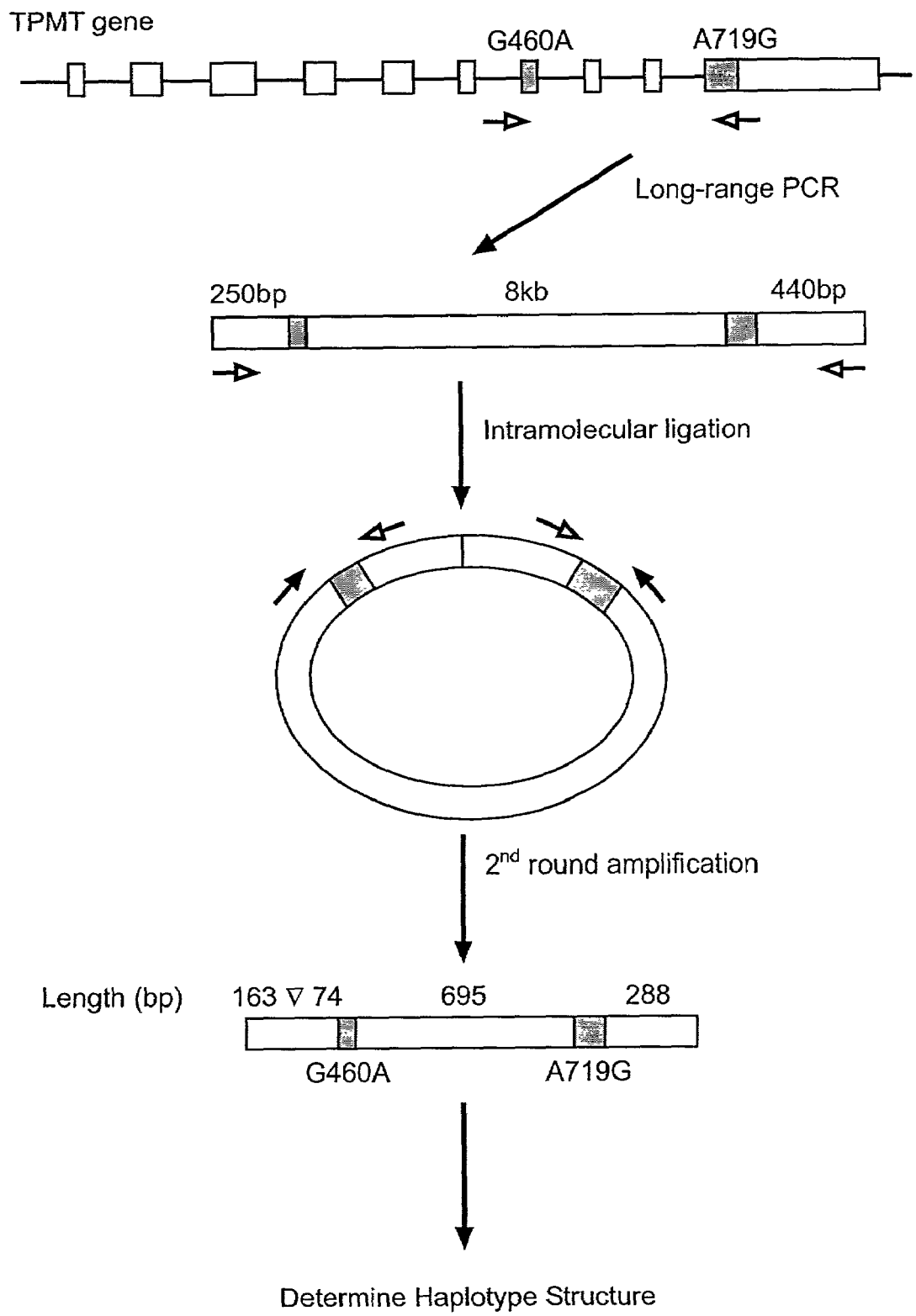
FIG. 1 is a schematic representation of a strategy for the determination of the haplotype structure of the human thiopurine S-methyltransferase (TPMT) gene. As indicated at the top of FIG. 1, the TPMT gene is known to possess two distal sites with single nucleotide polymorphisms (SNPs) (shaded regions labeled G460A and A719G). Within the TPMT gene, the two SNPs are separated by approximately 8 kb. The strategy for determining haplotype structure of the TPMT gene involves long-range PCR comprising both a DNA sample containing the TPMT gene and a first set of oligonucleotide primers (open-head arrows) designed for the amplification of the two SNPs and the region of the TPMT gene separating them. The resulting approximately 8.7 kb PCR product is then circularized via intramolecular ligation. The circular DNA molecule can be used directly to determine the haplotype structure of the TPMT gene by standard techniques known in the art, or as depicted in FIG. 1, the circular DNA molecule can be subjected to a second PCR amplification. The second PCR amplification involves the circular DNA molecule as a template and a second pair of oligonucleotide primers (closed-head arrows lying adjacent to the circular DNA). The second PCR product is approximately 1.2 kb and comprises both SNPs separated by 695 nucleotides. The haplotype structure of the second PCR product can then be determined by standard methods known in the art for SNPs that are separated by less than about 1 kilobase.

The invention provides methods for determining the haplotype structure of any contiguous DNA segment comprising two or more NPs. By "nucleotide polymorphism", or "NP", is intended a known variation in a DNA sequence at a particular location among contiguous DNA segments that are otherwise similar in sequence. Such contiguous DNA segments include, for example, a gene or any other portion of a chromosome. While the invention does not depend on NPs of any particular length, preferably such NPs are the result of a substitution, deletion, or insertion of 50 nucleotides or less, such as 40, 30, 20, 10, 5, or even 1 nucleotide. More preferably, such NPs are the result of a substitution of five nucleotides or less, such as 4, 3, 2, or even 1 nucleotide; a deletion of five nucleotides or less, such as 4, 3, 2, or even 1 nucleotide; and an insertion of five nucleotides or less, such as 4, 3, 2, or even 1 nucleotide. By "haplotype" is intended the nucleotide sequence of the NP. By "haplotype structure" is intended the haplotype of each NP of a contiguous DNA segment or an allele of a gene or other portion of a chromosome.

The genomes of all organisms undergo spontaneous mutation in the course of their continuing evolution generating variant forms of progenitor sequences (Gusella (1986) *Ann. Rev. Biochem.* 55: 831–854). A variant form of a gene may confer an evolutionary advantage or disadvantage relative to a progenitor form or may be neutral. In some instances, a variant form of the gene confers a lethal disadvantage and is not transmitted to subsequent generations of the organism. In other instances, a variant form of a gene confers an evolutionary advantage to the species and is eventually incorporated into the DNA of many or most members of the species and effectively becomes the progenitor or wild-type form. In many instances, both progenitor and variant form(s) survive and co-exist in a species population. The coexistence in a species population of multiple forms of a sequence at a particular location within a gene or other portion of chromosomal DNA gives rise to a nucleotide polymorphism for that particular site within the gene or chromosome. Accordingly, a nucleotide polymorphism includes the progenitor or wild-type sequences and all variants thereof that are known to occur at that particular location in the species population. The present invention involves determining the nucleotide sequences present at two or more polymorphic sites within a single contiguous DNA segment or allele of a gene.

The invention is drawn to methods for determining the haplotype structure of genes, particularly genes or contiguous DNA segments comprising at least two distantly spaced NPs. The methods find use in medicine in determining the differences in disease risk and treatment response between individual patients. The methods, however, are not limited to applications in medicine and can be used to determine the haplotype structure of a particular gene, or other contiguous DNA segment, within an organism having at least two distally spaced NPs. Thus, the methods of the invention find further use in the field of agriculture, particularly in the breeding of improved livestock and crop plants.

The methods involve the molecular haplotyping of contiguous DNA segments or genes that have two or more nucleotide polymorphisms (NPs) therein, particularly single nucleotide polymorphisms (SNPs). The methods find particular use in haplotyping genes that have two or more NPs, wherein at least two of the NPs are separated within the gene by more than one kilobase of DNA, although the methods can be used to haplotype genes with NPs separated by smaller lengths of 200 nucleotides or less. The methods of the invention bring the two NPs on the same allele of a gene into closer proximity allowing for the analysis of haplotype structure by methods known in the art including, but not limited to, RFLP analysis, single-strand conformational polymorphism analysis, heteroduplex analysis, oligonucleotide ligation and hybridization assays, PCR-RFLP, allele-specific amplification, single-molecule dilution, and coupled amplification and sequencing. In particular, the methods of the invention involve the use of PCR (polymerase chain reaction) to amplify a DNA fragment that comprises at least a portion of the gene of interest. Typically, the DNA sample that provides the templates for the PCR amplification comprises genomic DNA from a patient or organism of interest. Oligonucleotide primers are designed to amplify a DNA fragment that comprises at least two of the NPs.

For example, in a gene of interest comprising, in the 5'-to-3' direction, a first NP, an intervening DNA sequence and a second NP, a first pair of oligonucleotide primers are designed such that a fragment of the native gene that comprises both NPs and the intervening sequence as arranged in the gene can be amplified by PCR (see FIG. 1). The desired fragment also comprises additional DNA sequences in the native gene immediately 5' to the first NP and immediately 3' to the second NP and will encompass the annealing sites for the primers. While the invention does not depend on the length of these additional sequences, each of the additional sequences will typically be about 500, 400, 300, 200, 100, or 50 bases, or less.

In addition to being designed to amplify a DNA fragment corresponding to the first and second NPs and the intervening DNA sequence, each member of the first pair of oligonucleotide primers can also be designed to contain a restriction enzyme recognition site to facilitate circularization of the DNA fragment. Such restriction enzyme recognition sites are known to those of ordinary skill in the art and are recognized by restriction enzymes or restriction endonucleases that cleave DNA. Each of the primers will contain a 5' region that comprises the restriction enzyme recognition site and a 3' region that is capable of annealing to DNA sequences corresponding to those found in the gene of interest. The desired restriction enzyme recognition sites for use in the primers are ones that are not known to occur within the portion of the gene of interest that is to be amplified. Furthermore, the desired restriction enzyme recognition sites are those that are recognized by restriction enzymes that are known to produce DNA with "sticky ends" following cleavage. Such "sticky ends" are known in the art and comprise the ends of a linear, double-stranded DNA molecule, wherein one of the two strands of the molecule is one or several bases shorter than its complementary strand, resulting in a small region of single-stranded DNA.

The invention, however, does not depend on the use of primers containing restriction enzyme recognition sites, only that the amplified DNA fragment produced by PCR amplification can be circularized by intramolecular ligation. The amplified DNA fragment, for example, can be circularized by blunt-end ligation using methods known to those of ordinary skill in the art. Furthermore, it is recognized that a DNA fragment produced by PCR amplification with certain thermostable DNA polymerases, such as, for example, Taq polymerase, will typically contain an 3' overhang of one or more "A" nucleotides on each strand of the DNA fragment. Those of ordinary skill in the art will recognize that, before attempting the blunt-end ligation, it is desirable to eliminate such an overhang by incubating the DNA fragment under appropriate conditions in a solution comprising, for example, T4 DNA ligase.

Typically, for convenience, when primers containing restriction enzyme recognition sites are employed, both members of the first pair of primers will have the same restriction enzyme recognition site, although each can have a different restriction enzyme recognition site, if so desired. If each of the primers have different restriction enzyme recognition sites, the sites are ones that, upon cleavage by their respective restriction endonucleases, produce compatible "sticky ends" for ligation. In this manner, the cleaved DNA from the region corresponding to the first primer would anneal to cleaved DNA from the region corresponding to the second primer. The resulting annealed ends would be capable of being ligated by DNA ligase to form a circular DNA molecule.

Alternatively, a DNA fragment with such sticky ends can be produced by PCR amplification using mixed DNA/RNA primers (Colijee et al. *Nature Biotech* 18: 789–791 (2000). After the PCR amplification, the amplified fragments can be treated with a base or an RNAse to create 3' DNA overhangs suitable for ligation as described supra. While such DNA/RNA primers can be used to amplify any DNA fragment, they are particularly useful when, due to a preponderance of restriction enzyme sites within the intervening sequence separating the SNPs in the native gene, it is not possible to design PCR primers with suitable restriction enzyme recognition sites as described supra.

Following a PCR amplification with primers designed to contain restriction enzyme recognition sites, the amplified DNA fragment is incubated in the presence of restriction enzymes to cleave the fragment within or near the restriction enzyme recognition sites that are found at both ends of the fragment and which correspond to the regions of the oligonucleotide primers. The resulting cleaved fragment is then circularized by incubating the fragment in the presence of DNA ligase (see FIG. 1).

While the methods of the invention depend neither on any particular DNA ligase nor on any particular conditions for intramolecular DNA ligation, those skilled in the art will recognize that reaction conditions and components can be varied to enhance the production of the desired circular DNA molecule. Such conditions and components for intramolecular DNA ligation are known in the art. See, for example, Collins and Weissman (1984) *Proc. Natl. Acad. Sci. USA* 81:6812–6816; herein incorporated by reference.

Furthermore, it is recognized that following the ligation, any remaining linear DNA molecules can be eliminated by incubating the products of the ligation in the presence of a nuclease, such as, for example, Exonuclease III, which degrades linear DNA but not circular DNA. While typically such a nuclease incubation will not be necessary, the nuclease incubation can be used, if desired, to avoid any possible interference from linear DNA molecules in the subsequent determination of haplotype structure as disclosed herein.

Following ligation, the NPs on the circular DNA molecule are in much closer proximity than in the native gene or contiguous DNA segment and can be haplotyped using standard techniques known in the art. If desired, the circularized DNA molecule can then be subjected to PCR amplification with a second pair of oligonucleotide primers to produce a second DNA fragment (see FIG. 1). The second pair of oligonucleotide primers comprises a first primer designed to anneal to a region of DNA adjacent to the first NP and a second primer designed to anneal to a region of DNA adjacent to the second NP. The second set of primers is designed to amplify a second fragment of DNA comprising each of the NPs and the region of DNA that corresponds to the 5' and 3' ends of the amplified fragment produced in the first PCR amplification and ligated together as described above.

Following the second PCR amplification, the resulting linear DNA fragment contains the two NPs in closer proximity than in their original orientation. In genes with NPs that are separated by many kilobases of DNA, the methods of the invention bring the NPs on the same DNA molecule into much closer proximity than found in the original gene, while preserving the haplotype structure of a particular allele (FIG. 1). Thus, the methods of the invention allow for the unambiguous determination of haplotype structure of each of the alleles present at particular gene in a diploid organism. The fragment resulting from the second amplification can be used to haplotype the two NPs by methods known in the art including, but not limited to, restriction fragment-length polymorphism analysis, single-strand conformational polymorphism (SSCP) analysis (Orita et al. (1989) *Proc Natl. Acad. Sci. USA* 86:2766–2770) heteroduplex analysis (Prior et al. (1995) *Hum. Mutat.* 5:263–268), and oligonucleotide ligation (Nickerson et al. (1990) *Proc. Natl. Acad. Sci. USA* 87:8923–8927) and hybridization assays (Conner et al. (1983) *Proc. Natl. Acad. Sci. USA* 80:278–282); herein incorporated by reference.

Alternatively, instead of using the circular DNA molecules as templates for a second PCR amplification as described supra, the circular DNA molecules can be used directly in traditional Taq polymerase PCR-based strategies that are known in the art for haplotyping NPs in short DNA segments. Such strategies include, for example, PCR-RFLP, allele-specific amplification (ASA) (Ruano and Kidd (1989) *Nucleic Acids Res.* 17:8392), single-molecule dilution (SMD) (Ruano et al. (1990) *Proc. Natl. Acad. Sci. USA* 87:6296–6300), and coupled amplification and sequencing (CAS) (Ruano and Kidd (1991) *Nucleic Acids Res.* 19:6877–6882); all of which are herein incorporated by reference.

While certain methods of the invention involve PCR amplification with the circular DNA molecule as a template, the invention does not depend on such a PCR amplification for determining the haplotype structure of a gene of interest. The haplotype structure of the gene of interest can be determined directly from the circular DNA molecule using methods such as, for example, heteroduplex analysis (Prior et al. (1995) *Hum. Mutat.* 5:263–268), and oligonucleotide ligation (Nickerson et al. (1990) *Proc. Natl. Acad. Sci. USA* 87:8923–8927), and oligonucleotide hybridization assays (Conner et al. (1983) *Proc. Natl. Acad. Sci. USA* 80:278–282); all of which are herein incorporated by reference.

In one embodiment of the invention, a method for determining the haplotype structure of the human thiopurine S-methyltransferase (TPMT) gene is provided (see FIG. 1). Genetic polymorphism in the TPMT gene is known to affect the metabolism of widely used thiopurine medications. The genetic polymorphism is due to the presence of SNPs at two sites within the TPMT gene. The first SNP occurs at nucleotide 460, wherein a G in the wild-type allele is substituted with an A (G460A). The second SNP occurs at nucleotide 719, wherein an A in the wild-type allele is substituted with a G (A719G). The nucleotide positions of the SNPs indicated in FIG. 1 refer to the positions of the SNPs in the transcribed portions of the TPMT gene with intronic regions omitted. Within the TPMT gene, the first and second SNPs are separated by approximately 8 kb. Because of the large distance between the two SNPs in the TPMT gene, conventional methods of analyzing haplotype structure have proven ineffective, inefficient, or both. Long-range PCR was used to amplify a fragment of the TPMT gene comprising both SNPs and the eight-kilobase region of the gene that separates them. For the long-range PCR amplification, two different oligonucleotide primers were used. The primers (depicted as open-head arrows in FIG. 1) were designed to anneal to the specific sites within the TPMT gene and to serve as primers of the synthesis of a contiguous DNA fragment comprising both SNPs and the eight kilobase region between them. The first primer was designed to anneal to a region adjacent to and 5' of the first SNP. The second primer was designed to anneal to a region adjacent to and 3' of the second SNP. Each primer also included a restriction enzyme recognition site for the restriction enzyme BamHI. The BamHI recognition site was selected for inclusion in the primers because such BamHI recognition sites are not known to occur within the region of the TPMT gene between the annealing sites for the two PCR primers. Following PCR amplification, the amplified fragment was digested with BamHI and self-ligated to form a circular DNA molecule through the use of DNA ligase (see FIG. 1). Within the circular DNA molecule, the first and second SNPs were brought to within about 700 nucleotides of each other. The haplotype structure of the TPMT gene was then determined by RFLP analysis of an approximately 1.2 kilobase DNA fragment that was produced by a second PCR amplification using the circular DNA as a template (see FIG. 1). For this PCR amplification, primers (depicted as closed-head arrows lying adjacent to the circular DNA depicted in FIG. 1) were designed to amplify the approximately 1.2 kilobase DNA fragment containing the two SNPs. Thus, the method of the invention was used to bring the two SNPs into closer proximity than in the native gene and allowed the haplotype structure of the TPMT gene to be determined by existing methods that could only previously be used for SNPs that were known to occur within close proximity of each other, preferably less than about 1 kilobase.

The methods of invention also find use in determining the haplotype structure of a gene with three or more NPs. In this manner, all of the NPs within a contiguous DNA segment, gene of interest, or other portion of a chromosome can be amplified as part of a single DNA fragment using a single long-range PCR amplification, coupled with subsequent ligation and PCR amplification (repeated until all NPs are brought into proximity within one another), and RFLP analysis as described supra. Alternatively, multiple overlapping long-range PCR amplifications can be performed in which one or more NPs are contained within sequential PCR fragments. Such an approach can be used when the SNPs are separated by kilobase distances within the native gene. For example, a gene having in the 5'-to-3' direction a first, a second, and a third NP can be haploptyped by using the method described supra to bring the first and second NPs into close proximity on the same molecule. The haplotype structure of the first and second NPs can then be determined as described supra. In a like manner, the second and third NPs can also be brought into close proximity on the same DNA molecule and haplotype structure of the second and third NPs determined. From the two separate determinations, the haplotype structure with respect to all three NPs is revealed. Thus, the methods of the invention can be used to determine the haplotype structure of genes with multiple heterozygous or homozygous NPs.

The invention also provides kits for determining the haplotype structure of particular genes. The kits find use in determining the haplotype structure of a contiguous DNA segment, gene of interest, or other portion of a chromosome by the methods of the invention described supra. The kits comprise the first pair of PCR primers described supra, which are designed to amplify in a 5'-to-3' direction a first NP, an intervening DNA sequence, and a second NP. The kits further comprise one or more thermostable DNA polymerases suitable for use in PCR amplification and a means for determining the haplotype structure of each NP. The kits can also optionally include DNA ligase and one or more restriction enzymes that are known to cleave DNA at or near a restriction enzyme cleavage site within the primers. The kits may also contain reagents for performing the PCR amplification reaction and the ligation reaction, including, but not limited to, buffers, additional primers, nucleotide triphosphates, enzymes, and the like. The components of the kits can be packaged together in a common container, optionally including instructions for performing a specific embodiment of the methods of the invention.

The kits of the invention can contain a means for determining haplotype structure of each NP on the circularized DNA. Such means include, but are not limited to, RFLP analysis, single-strand conformational polymorphism analysis (Orita et al. (1989) *Proc. Natl. Acad. Sci. USA* 86:2766–2770) heteroduplex analysis (Prior et al. (1995) *Hum Mutat.* 5:263–268), and oligonucleotide ligation (Nickerson et al. (1990) *Proc. Natl. Acad. Sci. USA* 87:8923–8927), hybridization assays (Conner et al. (1983) *Proc. Natl. Acad. Sci. USA* 80:278–282), and traditional Taq polymerase PCR-based strategies, such as PCR-RFLP, allele-specific amplification (Ruano and Kidd (1989) *Nucleic Acids Res.* 17:8392), single-molecule dilution (Ruano et al. (1990) *Proc. Natl. Acad. Sci. USA* SA 87:6296–6300), and coupled amplification and sequencing (Ruano and Kidd (1991) *Nucleic Acids Res.* 19:6877–6882). If desired, the kit can contain instructions and some or all of the necessary components for a means for determining haplotype structure. Such components include, but are not limited to, buffers, primers for PCR amplifications, restriction enzymes, salts, deoxyribonucleotides, thermostable DNA polymerases, and the like.

The methods of the invention do not depend on any two NPs being separated by any particular distance within a gene of interest. The distance between two NPs can be about 200, 300, 400, 500, 600, 700, 800, 900 or 1000 bases. However, the methods of the invention find particular use in haplotyping NPs that are separated by one or more kilobases. In particular, the preferred methods involve two NPs separated by about 1, 2, 3, 4, 5, 6, 7, 8, 9, 10, 15, 20, 25, 30, 35, 40 or more kilobases.

The invention also provides circular DNA molecules that find use in determining the haplotype structure of genes with two or more NPs. The circular DNA molecules comprise at least two SNPs that are in closer proximity to each other than in the native gene or chromosome in the genome of an organism. Such NPs are brought into closer proximity to each other by the intramolecular ligation of linear DNA containing the two NPs.

In certain embodiments of the invention, the methods can involve PCR amplification of long templates, particularly templates greater than about ten kilobases in length. Such methods are known in the art and may be referred to as long PCR or long-range PCR. Generally, such methods employ a combination of two different thermostable DNA polymerases to amplify the target DNA. Additionally, such PCR methods typically employ reaction conditions that favor the amplification of long templates and relatively longer extension periods than routinely used for the amplification of shorter templates. See, for example, Cheng et al. ((1994) *Proc. Natl. Acad. Sci. USA* 91:5695–5699); herein incorporated by reference.

The methods of the invention can be used to determine the haplotype structure of any gene that has two or more distantly spaced NPs therein. Preferred genes include those for which haplotype structure has been shown to be more important in than individual NPs in assessing disease risk and treatment response in humans. Such genes include, for example, genes encoding TPMT, beta2 receptor, apolipoprotein E (apoE), OPRM1, and interleukin-4 (IL-4) receptor alpha.

While the invention has been described for determining the haplotype structure of genes with two or more NPs, the use of the term "gene" is not intended to limit the invention to two or more NPs within a single gene. Thus, the invention does not depend on the two NPs being within the same gene or allele thereof, only that the two NPs occur on the same DNA molecule and are separated from each other by an intervening DNA sequence such that both NPs and the intervening DNA sequence can be amplified in a single PCR amplification to produce a single amplified DNA fragment. Such an amplified fragment will faithfully reflect the native arrangement of the NPs and the intervening DNA sequence within the template DNA molecule. Such template DNA molecules include, for example, chromosomes and genes therein. Thus, the two NPs can reside in different genes on the same chromosome or even in intragenic regions of a chromosome.

The methods of the invention involve the use of PCR. Oligonucleotide primers can be designed for use in PCR reactions to amplify corresponding DNA sequences from genomic DNA or cDNA extracted from any organism of interest. Methods for designing PCR primers are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Other known methods of PCR that can be used in the methods of the invention include, but are not limited to, methods using paired primers, nested primers, single specific primers, degenerate primers, gene-specific primers, mixed DNA/RNA primers, vector-specific primers, partially-mismatched primers, and the like.

In addition to PCR amplification, the methods of the invention can involve various techniques of molecular biology including, for example, DNA isolation, particularly genomic DNA isolation, digestion of DNA by restriction enzymes and nucleases, DNA ligation, DNA sequencing, gel electrophoresis and the like. Such techniques are generally known in the art and are disclosed, for example, in Sambrook et al. (1989) *Molecular Cloning: A Laboratory Manual* (2d ed., Cold Spring Harbor Laboratory Press, Plainview, N.Y.).

The following examples are offered by way of illustration and not by way of limitation.

Experimental

The invention discloses novel methods that reliably and easily bring distantly located nucleotide polymorphisms (NPs) into close proximity on a single PCR amplified fragment, thereby permitting haplotype structure to be directly determined in a manner analogous to that commonly used for haplotyping closely positioned single nucleotide polymorphisms (SNPs). The novel methods involve the use of PCR, particularly LR-PCR, followed by intramolecular ligation (circularization) that brings such NPs into physical proximity that can be assessed by PCR-RFLP analysis. An example of the use of the methods of the invention is disclosed herein for the human TPMT gene and its common allelic variants (see FIG. 1).

The new strategy to directly determine haplotype structure, depicted in FIG. 1, was applied to genomic DNA samples isolated from two individuals who were multiply heterozygous at two SNP sites in the human TPMT gene (either TPMT*1/*3A or TPMT*3B/*3C genotype), one each with a TPMT*1/*3C and TPMT*1/*1 genotype, and positive control DNA with TPMT*3B/*3C or TPMT *3A/*1 genotype. The authenticity of the LR-PCR products was verified by cloning and sequencing. Results achieved with the new haplotyping method were concordant with results achieved by conventional genotyping methods (Yates et al. (1997) *Ann. Intern. Med.*, 126:608–614), but the new method permitted determination of TPMT*3 haplotype by establishing whether the 460 and 719 mutations were on the same (*3A) or opposite (3B/*3C) alleles. Both of the multiply heterozygous genomic DNA samples were found to be TPMT*3A/*1 genotypes, with an RFLP pattern distinct from TPMT*3B/*3C genomic DNA.

Thus, the new method provides a simple and reliable method to directly determine haplotype structure for NPs, particularly SNPs located kilobases apart in genomic DNA. This method eliminates the shortcomings of current methods that are not able to determine such haplotype structures or are laborious, require complex equipment, or can not unambiguously determine haplotypes for such SNPs. The potential clinical and scientific importance of unambiguously determining such haplotype structures is illustrated by TPMT, a common genetic polymorphism affecting the metabolism of widely used thiopurine medications (mercaptopurine, thioguanine, azathioprine) (Krynetski and Evans (1998) *Am. J. Hum. Gen.* 63:11–16). TPMT activity is inherited as an autosomal codominant trait, displaying genetic polymorphism in Caucasian, Asian, African, and African-American populations. About 90% of individuals inherit high TPMT activity, 10% intermediate activity due to heterozygosity at the TPMT locus, and 1 in 300 inherit TPMT deficiency. TPMT deficient patients accumulate extremely high levels of thioguanine nucleotides (TGN) in erythrocytes, if treated with conventional doses of thiopurines (Krynetski and Evans (1998) *Am. J. Hum. Gen.* 63:11–16). These patients are at high risk for severe hematopoietic toxicity due to excess accumulation of TGN, resulting in leukopenia, thrombopenia, and anemia, which can be fatal. However, these toxicities can be avoided if thiopurine dosages are decreased by 90–95%, permitting these patients to tolerate thiopurine therapy without acute toxicity (Evans et al. (1991) *J. Pediatr.,* 119:985–989). Patients who are heterozygous at the TPMT gene locus have intermediate TPMT activity and intermediate intolerance to thiopurine medications, generally requiring only modest dose reductions (Relling et al. (1999) *J. Natl. Cancer Inst.* 91:2001–2008).

One class of variant TPMT alleles (i.e., TPMT*3), comprise the most prevalent mutant alleles in Caucasian (Yates et al. (1997) *Ann. Intern. Med.,* 126:608–614), African-American (Hon et al. (1999) *Hum. Mol. Genet.* 8:371–376), African (Ameyaw et al. (1999) *Hum. Mol. Gen.* 8:367–370), and Asian (Ameyaw et al. (1999) *Hum. Mol. Gen.* 8:367–370) populations. Mutant alleles in the TPMT*3 family contain one or both of two SNPs in their open reading frame, a G to A transition in exon 7 (G460A) and an A to G transition in exon 10 (A719G), both of which lead to amino acid substitutions (Tai et al. (1996) *Am. J. Human Gen.* 58:694–702). TPMT*3A contains both mutations on the same TPMT allele, and is the predominant TPMT mutant allele in Caucasians (Yates et al. (1997) *Ann. Intern. Med.,* 126:608–614; Ameyaw et al. (1999) *Hum. Mol. Gen.* 8:367–370). TPMT*3C contains only the A719G mutation, and is the most common TPMT mutant allele in African (Ameyaw et al. (1999) *Hum. Mol. Gen.* 8:367–370), African-American (Hon et al. (1999) *Hum. Mol. Genet.* 8:371–376) and Asian (Collie-Duguid et al. (1999) *Pharmacogenetics* 9:37–42) populations. The TPMT*3B allele has been reported to occur rarely in these populations (Yan et al. (2000) *Clin Pharmcol Ther.* 68:210–219), and its presence confounds genotyping methods that are not haplotype specific. Each of these mutant alleles encodes TPMT proteins that undergo rapid proteolysis (Tai et al. (1997)) *Proc. Natl. Acad. Sci. USA* 94:6444–6449; Tai et al. (1999) *Pharmacogenetics* 9:641–650), leading to low or undetectable TPMT protein levels in patients. Heterozygotes who inherit one of these mutant alleles (*3A, *3B, *3C) and one wildtype allele (*1) have intermediate TPMT activity, and intermediate intolerance to thiopurine therapy (Relling et al. (1999) *J. Natl. Cancer Inst.* 91:2001–2008). Compound heterozygotes, with a TPMT*3B/*3C genotype, one allele containing only the G460A mutation and the other containing only the A719G mutation, would be TPMT-deficient. Thus, it is critical to determine whether individuals who are heterozygous at both the 460 and 719 nucleotides, have these mutations on the same (*1/*3A genotype) or different (*3B/*3C genotype) TPMT alleles, as their risk of toxicity and thiopurine dosages will be markedly different (i.e., 5–10 fold). The same haplotype-specific differences in treatment response have been observed for other medications (Drysdale et al. (2000) *Proc. Natl. Acad. Sci. USA* 97:10483–8), and is likely to pertain when multiple haplotypes exist for a polymorphic gene.

The new method represents a simple strategy to determine haplotype structure for NPs located kilobases apart, exemplified with two common SNPs in the human TPMT gene. These two SNPs lie about 8 kb apart in the human TPMT gene, yet it is possible to amplify both SNP locations in the same long-PCR fragment. Subsequent intramolecular ligation of this fragment places the two SNP sites within 695 nucleotides of each other, permitting a second round amplification of a shorter fragment, followed by RFLP analysis (or allele-specific amplification) to determine whether the mutations reside on the same or opposite alleles. Moreover, this method requires instrumentation and reagents that are widely available, utilizes genomic DNA, and is easy to perform. The method is also applicable when more than two SNPs define haplotype structure, by either encompassing all SNPs in one initial long-PCR fragment (coupled with subsequent PCR, ligation, and RFLP analysis), or by performing multiple overlapping long-PCR amplifications in which two or more SNPs are contained within sequential PCR fragments. This new method thus provides a simple yet robust tool for determining haplotype structures of any gene in which SNPs lie within about 35 kb of genomic DNA (the limits of LR-PCR), providing a widely applicable molecular diagnostic that will enhance pharmacogenomic and epidemiological studies when haplotype structure is the principal determinant of inherited phenotypes.

Experimental Protocol

Preparation of DNA Samples. Whole blood was obtained from healthy volunteers or patients from St. Jude Children's Research Hospital who had acute lymphoblastic leukemia (ALL). Each subject provided informed consent, and the research protocol and consent were approved by the Institutional Review Board (IRB). All DNA was extracted and purified using Qiagen Genomic Tips, QIAamp blood kit, or Tri-Reagent; all three methods yielded equally suitable DNA.

Long-range PCR. Long-PCR reactions were performed on 100 ng of purified Genomic DNA with primers LF4B and LR4B (shown in Table 1) using the Expand Long Template System (Roche). Primer LF4B is homologous to an intronic sequence flanking exon 7 on the 5'-end, to avoid amplification of the TPMT pseudogene. Reaction conditions were according to manufacturer's recommendations with the following exceptions: PCR reaction mixture was subjected to denaturation at 94° C. for 2 minutes after which the reaction mixture was held at 69° C. for 5 minutes to allow for specific primer annealing. Polymerase enzyme mixture was withheld until completion of this step. Upon addition of enzyme, reaction conditions were carried out according to manufacturer recommendations except that the annealing temperature was 67.5° C. PCR products (9 kb in length) were then sequenced or subjected to ligation and PCR-RFLP analysis, as described below.

Sequencing of PCR Products. PCR products to be sequenced were cloned into pCR2.1 plasmids with the TOPO TA Cloning Kit (Invitrogen), to keep alleles separate. Plasmids were purified with QIAprep Plasmid Purification kits (Qiagen) and checked for inserts. Bi-directional sequencing of plasmids was performed with the universal M13 forward and reverse primers by fluorescent dye-terminator cycle sequencing using an ABI prism 3700 DNA Analyzer, in the Hartwell Center for Biotechnology at St. Jude. The University of Wisconsin Genetics Computer Group software package was used to analyze all sequence data.

Intramolecular Ligation of PCR Products. Intramolecular ligation of linear 9 kb Long-PCR fragments into circular molecules was carried out according to conditions described by others (Collins and Weissman (1984) *Proc. Natl. Acad. Sci. USA* 81:6812–6815). This was necessary to bring the two TPMT*3 mutation sites close enough together (659 nucleotides) that a sequence recognized by these restriction enzymes used in the subsequent RFLP analyses would not be present between them, which would otherwise confound haplotyping results. Briefly, PCR products were digested with BamHI to produce sticky ends. This was made possible by the addition of BamHI sites onto the 5'-ends of primers LF4B and LR4B, and because no BamHI sites exist within the amplified region. The digested fragments were placed into 500 μl reaction volumes containing 10 Units of T4 DNA Ligase (Gibco, Life Sciences, US), incubated at 14° C. overnight (14–16 hrs) and then subjected to second round PCR amplification.

Second Round PCR and RFLP Analysis. The circular ligation products were purified into 50 μμl of water with Suprec-02 cartridges (TaKaRa). This mixture was diluted to 1 ml with water, and 0.5 μl of this was used for amplification with 225 pmol each of primers 7F and 4R, using the Expand Long Template System. It was important to keep the ratio of primer to template concentration high to avoid truncated products containing allelic mutations serving as primers. In the few cases where this occurred, the template was diluted to more than 1 ml, which eliminated truncated products serving as primers in these samples. A 68° C. annealing temperature (with 0.1° C. reduction per PCR cycle) was the only other departure from the manufacturer's recommendations. The resulting 1,220 base-pair products were then digested simultaneously with AccI and MwoI in NE buffer 4 (New England Biolabs) and visualized on a 2% agarose gel containing ethidium bromide. The G460A mutation eliminates a MwoI restriction site while the A719G mutation introduces an AccI restriction site. A genotype of *3A/*1 displays an electrophoresis banding pattern containing fragments of 983 bases (*1) and 769 bases (*3A), whereas a *3B/*3C genotype produces bands of 1,057 (*3B) and 695 (*3C) bases. All other bands present (288, 163, 74 bases) are identical in both genotypes.

Construction of Positive Controls. TPMT*3A/*1 controls for second-round amplification and restriction digestion were genomic DNA isolated from a human cell line with a cDNA sequence verified TPMT*3A/*1 genotype. TPMT*3B and TPMT*3C templates were created from PCR-mediated site-directed mutagenesis of 100 ng of high quality human genomic DNA (Clontec), and sequence verified.

TABLE 1

5'–3' Sequences of Primers Used for PCR Amplifications

| | |
|---|---|
| LF4B[e] | GC<u>GGATCC</u>GAGGCTGCTGCCACAGGCTCCTAAAAC |
| LR4B | GC<u>GGATCC</u>CACTCCAGGTTGGGCAACAAGAACGAAACTCC |
| 7F | CAAGCCTTATAGCCTTACACCCAGG |
| 4R | GAGACAGAGTTTCACCATCTTGG |

[e]Restriction enzyme recognition sequences are underlined.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for determining the haplotype structure of a contiguous DNA segment comprising a first nucleotide polymorphism (NP) and a second NP separated by at least 200 nucleotides, said method comprising:
   (a) obtaining a DNA sample comprising said contiguous DNA segment;
   (b) using said DNA sample as a template for polymerase chain reaction (PCR) amplification of a DNA fragment comprising said contiguous DNA segment,
   wherein the PCR amplification is performed with
   a first primer capable of annealing to a region adjacent to the first NP and distal to the second NP and
   a second primer capable of annealing to a region adjacent to the second NP and distal to the first NP;
   (c) ligating the ends of said DNA fragment to each other so as to produce a circular DNA molecule, wherein said first NP and said second NP are brought into closer proximity on said circular DNA molecule relative to said contiguous DNA segment; and
   (d) determining the haplotype of said first NP and said second NP.

2. The method of claim 1 wherein said first NP and said second NP are separated by at least 1000 nucleotides.

3. The method of claim 2 wherein said first NP and said second NP are separated by at least 10,000 nucleotides.

4. The method of claim 3 wherein said first NP and said second NP are separated by at least 30,000 nucleotides.

5. The method of claim 1 wherein said first NP and said second NP are selected from the group consisting of a substitution of five nucleotides or less, a deletion of five nucleotides or less, and an insertion of five nucleotides or less.

6. The method of claim 5 wherein said first NP and said second NP each consist of a single nucleotide substitution.

7. The method of claim 1 wherein one or more additional NPs are located between said first NP and said second NP.

8. The method of claim 7 comprising the additional step of determining the haplotype of said one or more additional NPs.

9. The method of claim 1 wherein said nucleic acid sample is from a human source.

10. The method of claim 1 wherein the fragment of step (b) is obtained by amplification of said segment from said DNA sample using long-range polymerase chain reaction (LR-PCR).

11. The method of claim 1 wherein the fragment of step (b) is cleaved using a restriction enzyme that does not cleave any nucleotide sequences occurring between said first NP and said second NP on said contiguous DNA segment.

12. The method of claim 1 wherein the haplotype of said first NP and said second NP on said circular DNA molecule is detected by restriction fragment analysis of said circularized segment or of a PCR amplification product using said circular DNA molecule as a template.

13. The method of claim 1 wherein the haplotype of said first NP and said second NP is detected by PCR amplification using primers whose ability to amplify segments from said circular DNA molecule is dependent upon the presence or absence of a particular haplotype at said first NP and said second NP.

14. The method of claim 1 wherein said first NP and said second NP are located in the same gene.

15. The method of claim 14 wherein the haplotype of each allele of said gene is determined.

16. The method of claim 14, wherein at least one of said first NP and said second NP is associated with a clinically relevant phenotype.

17. The method of claim 14, wherein said gene is the TPMT gene.

18. The method of claim 14, wherein said gene is selected from the group consisting of genes encoding beta2 receptor, apoE, OPRM1, and IL-4 receptor alpha.

19. A method for determining the haplotype structure of a contiguous DNA segment comprising a first nucleotide polymorphism (NP) and a second NP separated by at least 200 nucleotides, said method comprising:
  (a) obtaining a DNA sample comprising said contiguous DNA segment, wherein the DNA segment further comprises
    a DNA sequence immediately 5' to the first NP that encompasses an annealing site for a primer and
    a DNA sequence immediately 3' to the second NP that encompasses an annealing site for a primer;
  (b) using said DNA sample as a template for polymerase chain reaction (PCR) amplification utilizing said primers of a DNA fragment comprising said contiguous DNA segment;
  (c) ligating the ends of said DNA fragment to each other so as to produce a circular DNA molecule, wherein said first NP and said second NP are brought into closer proximity on said circular DNA molecule relative to said contiguous DNA segment; and
  (d) determining the haplotype of said first NP and said second NP.

20. The method of 19, wherein the DNA sequence immediately 5' to the first NP has a length selected from the group consisting of:
  less than 500, less than 400, less than 300, less than 200, less than 100, or less than 50 bases long; and,
  wherein the DNA sequence immediately 3' to the second NP has a length selected from the group consisting of:
  less than 500, less than 400, less than 300, less than 200, less than 100, or less than 50 bases long.

* * * * *